(12) United States Patent
Regensburger

(10) Patent No.: US 11,210,819 B2
(45) Date of Patent: Dec. 28, 2021

(54) MOTION CORRECTION OF A RECONSTRUCTED THREE-DIMENSIONAL IMAGE DATASET

(71) Applicant: Siemens Healthcare GmbH, Erlangen (DE)

(72) Inventor: Alois Regensburger, Erlangen (DE)

(73) Assignee: Siemens Healthcare GmbH, Erlangen (DE)

(*) Notice: Subject to any disclaimer, the term of this patent is extended or adjusted under 35 U.S.C. 154(b) by 140 days.

(21) Appl. No.: 16/572,429

(22) Filed: Sep. 16, 2019

(65) Prior Publication Data

US 2020/0090380 A1  Mar. 19, 2020

(30) Foreign Application Priority Data

Sep. 19, 2018  (EP) ..................................... 18195337

(51) Int. Cl.
   *G06T 11/00* (2006.01)
   *G06T 7/73* (2017.01)
   (Continued)

(52) U.S. Cl.
   CPC ............ *G06T 11/005* (2013.01); *A61B 1/273* (2013.01); *A61B 6/12* (2013.01); *A61B 6/4441* (2013.01);
   (Continued)

(58) Field of Classification Search
   CPC ....... A61B 6/4014; A61B 6/12; A61B 6/5264; A61B 1/273; A61B 6/4441; A61B 6/486;
   (Continued)

(56) References Cited

U.S. PATENT DOCUMENTS 9,186,087 B2   11/2015  Liao
2005/0085715 A1  4/2005  Dukesherer
(Continued)

FOREIGN PATENT DOCUMENTS

DE  102012202648 B3  7/2013
DE  102013202313 A1  8/2014
(Continued)

OTHER PUBLICATIONS

Heimann, Tobias, et al. "Real-time ultrasound transducer localization in fluoroscopy images by transfer learning from synthetic training data." Medical image analysis 18.8 (2014): 1320-1328.
(Continued)

*Primary Examiner* — Brenda C Bernardi
(74) *Attorney, Agent, or Firm* — Lempia Summerfield Katz LLC

(57) ABSTRACT

Motion correction of a three-dimensional (3D) image dataset reconstructed from a plurality of two-dimensional (2D) projection images acquired by an X-ray device is provided. In order to acquire the projection images, each of two acquisition assemblies covers an angular range of projection angles, and pairs of projection images of a region under examination are acquired at least substantially simultaneously at each acquisition time instant. For each pair of projection images, at least one marker object lying in the region under examination is automatically localized in order to determine 2D location information. 3D position information about the marker object is determined using acquisition geometries of the respective pair of projection images. Motion information describing a motion profile of the marker object over the acquisition period is ascertained from the position information at different acquisition time instants, and the motion information is used for motion correction of the image dataset.

16 Claims, 3 Drawing Sheets

(51) Int. Cl.
  *G06T 7/246* (2017.01)
  *A61B 1/273* (2006.01)
  *A61B 6/12* (2006.01)
  *A61B 6/00* (2006.01)

(52) U.S. Cl.
  CPC ............ *A61B 6/486* (2013.01); *A61B 6/5264* (2013.01); *G06T 7/248* (2017.01); *G06T 7/74* (2017.01); *G06T 2207/10081* (2013.01); *G06T 2207/30204* (2013.01)

(58) Field of Classification Search
  CPC ..... A61B 6/0492; G06T 7/248; G06T 11/005; G06T 7/74; G06T 2207/30204; G06T 2207/10081
  See application file for complete search history.

(56) References Cited

U.S. PATENT DOCUMENTS

| | | |
|---|---|---|
| 2014/0226891 A1 | 8/2014 | Kunze |
| 2016/0135941 A1* | 5/2016 | Binmoeller .............. A61F 2/04 623/23.7 |
| 2017/0273665 A1 | 9/2017 | Kapoor |
| 2018/0008222 A1 | 1/2018 | Chen |

FOREIGN PATENT DOCUMENTS

| | | |
|---|---|---|
| EP | 1523951 A2 | 4/2005 |
| WO | WO2016134980 A1 | 9/2016 |

OTHER PUBLICATIONS

Rit, Simon, et al. "On-the-fly motion-compensated cone-beam CT using an a priori model of the respiratory motion." Medical physics 36.6Part1 (2009): 2283-2296.

Shechter, Guy, et al. "Prospective motion correction of X-ray images for coronary interventions." IEEE Transactions on Medical Imaging 24.4 (2005): 441-450.

Sindel, Aline, et al. "Respiratory Motion Compensation for C-Arm CT Liver Imaging." Bildverarbeitung für die Medizin 2015. Springer Vieweg, Berlin, Heidelberg, 2015. 221-226.

Syben, Christopher, et al. "Joint calibration and motion estimation in weight-bearing cone-beam CT of the knee joint using fiducial markers." 2017 IEEE 14th International Symposium on Biomedical Imaging (ISBI 2017). IEEE, 2017. pp. 494-497.

Rohkohl, Christopher, et al. "Interventional 4D motion estimation and reconstruction of cardiac vasculature without motion periodicity assumption." Medical Image Analysis 14.5 (2010): 687-694.

European Search Report for European Patent Application No. 18195337.3-1124 dated Mar. 27, 2019.

* cited by examiner

MOTION CORRECTION OF A RECONSTRUCTED THREE-DIMENSIONAL IMAGE DATASET

This application claims the benefit of EP 18195337.3, filed on Sep. 19, 2018, which is hereby incorporated by reference in its entirety.

BACKGROUND

The present embodiments relate to motion correction of a three-dimensional (3D) image dataset reconstructed from a plurality of two-dimensional (2D) projection images that are acquired by an X-ray device.

As is generally known, it is possible to reconstruct (e.g., by filtered backprojection and/or algebraic reconstruction) from two-dimensional X-ray projection images that have been acquired in different acquisition geometries (e.g., at different projection angles) from an X-ray device, three-dimensional image datasets of the region under examination that is visible in the projection images. Although it is also known to use computed tomography X-ray devices, in which the acquisition assembly including an X-ray source and an X-ray detector may cycle extremely quickly through a range of projection angles to be covered, it is increasingly common to generate three-dimensional image datasets also at workstations at which, for example, an X-ray device having a C-arm is available (e.g., as part of minimally invasive interventions on the patient; where the progress of an examination and/or treatment is meant to be monitored). In addition, the applicant uses the name "DynaCT" to refer to the acquisition of projection images using a C-arm X-ray device and the reconstruction of a three-dimensional image dataset therefrom.

A fundamental problem with the time-staggered acquisition of two-dimensional projection images by an X-ray device is that movements of the patient (e.g., periodic movements such as respiratory movement and/or the heartbeat and also other patient movements) cause a displacement of anatomical structures to be acquired in the region under examination, which may result in artifacts/indistinct reproduction of anatomical structures (e.g., "blurring") and, in extreme cases, may render the three-dimensional image dataset unusable for diagnostic or other analysis. Therefore, various approaches have already been suggested in the prior art for minimizing patient movements during the acquisition of the projection images and/or for reducing or even entirely preventing motion artifacts in the three-dimensional image dataset (e.g., motion correction).

A first approach relates to avoiding respiratory movements. This may be done, for example, by stopping patient respiration temporarily under general anesthetic, or alternatively by asking a cooperative patient who is not under anesthetic to hold their breath actively for the period in which the projection images are acquired. Neither procedure may always be used in practice, and both relate only to respiratory movement.

An article by C. Syben et al., "Joint calibration and motion estimation in weight-bearing cone-beam CT of the knee joint using fiducial markers," 2017 IEEE 14th International Symposium on Biomedical Imaging (ISBI 2017), Melbourne, VIC, 2017, pp. 494-497. doi: 10.1109/ISBI.2017.7950568, proposes tracking reference markers as the knee moves during acquisition of the projection images.

Another article, "Respiratory Motion Compensation for C-Arm CT Liver Imaging," by A. Sindel et al., in Handels H., Deserno T., Meinzer H P., Tolxdorff T. (eds) "Bildverarbeitung für die Medizin 2015. Informatik aktuell" ("Image processing for medicine 2015. Computing today"), Springer Vieweg, Berlin, Heidelberg, proposes tracking visible structures in the projection images over an acquisition period.

Finally, an article by S. Rit et al., "On-the-fly motion-compensated cone-beam CT using an a priori model of the respiratory motion," Med. Phys., 36: 2283-2296, doi: 10.1118/1.3115691, also proposes acquiring the movements of a respiratory cycle in advance in order then to perform appropriate compensation. This does, however, assume very stable and regular breathing, which is often not the case, especially for patients under weak sedation.

The problem with the aforementioned approaches of tracking visible structures and/or reference markers is that only two-dimensional position information that exists at successive time instants and also with regard to different acquisition geometries (e.g., different projection angles) is obtained, and therefore, may not be correlated directly without error.

DE 10 2013 202 313 A1 relates to a method and a device for correcting motion artifacts in a computed tomography image. This document proposes initially reconstructing a preliminary three-dimensional computed tomography image in order to determine a mean position of a region under examination. Then, an optimization method is used to estimate, using at least one image volume block formed from definable projection images, the motion of the region under examination of the subject under examination in the at least one image volume block. A similar approach, which is also image-based and has been proposed elsewhere, likewise relates to an initial three-dimensional reconstruction of a high-contrast object (e.g., of a contrast-enhanced hepatic arterial tree) and seeks to estimate iteratively, by registering the individual two-dimensional projection images with the three-dimensional object, the motion in the projection image concerned. A motion field over time may be calculated therefrom, which is then compensated in the projection images, based on which another three-dimensional reconstruction that is motion-suppressed and of higher quality is performed.

These image-based approaches again have the problem that only two-dimensional information is available in the projection image at any instant in time, and also that the image-based approaches are based on a pre-generated three-dimensional reconstruction dataset that is not motion-corrected and therefore also may already contain errors.

US 2017/0273665 A1 relates to determining the pose of an ultrasound transducer. Inertial measurement units are positioned on the ultrasound transducer, which are meant to be combined with other position sensors (e.g., X-ray) in order to improve the accuracy and/or the rate at which the pose information is available. In addition, reference markers have already been proposed in the context of ultrasound imaging. The reference markers may be used to determine from a single fluoroscopy acquisition an orientation of a TEE sensor; for details, see the article by Tobias Heimann et al., "Real-time ultrasound transducer localization in fluoroscopy images by transfer learning from synthetic training data," Medical image analysis, Vol. 18, Issue 8, pages 1320 to 1328.

SUMMARY AND DESCRIPTION

The scope of the present invention is defined solely by the appended claims and is not affected to any degree by the statements within this summary.

The present embodiments may obviate one or more of the drawbacks or limitations in the related art. For example, improved motion correction is defined for image datasets to be reconstructed from two-dimensional (2D) projection images acquired over a time period.

The following acts are provided according to one or more of the present embodiments. A biplane X-ray device having two acquisition assemblies that measure at an angular offset (e.g., of 90°) is used. In order to acquire the projection images, each of the acquisition assemblies covers an angular range of projection angles, and pairs of projection images of the region under examination are acquired at least substantially simultaneously at each acquisition time instant. For each pair of projection images, at least one marker object lying in the region under examination and imaged in the projection images is automatically localized in order to determine two-dimensional location information. Three-dimensional position information about the marker object is determined using the acquisition geometries of the particular pair of projection images. The acquisition geometries are defined by the projection angles. Motion information describing a motion profile of the marker object over the acquisition period is ascertained from the position information at different acquisition time instants—. The motion information is used for motion correction of the image dataset.

In the present embodiments, a biplane X-ray device that allows projection images to be acquired at least substantially simultaneously using different acquisition geometries (e.g., specifically using different projection angles) is used. The biplane X-ray device may be a biplane X-ray device that has two C-arms, on each of which an X-ray detector and an X-ray source are arranged opposite one another to form one acquisition assembly in each case. The two planes of the biplane X-ray device may be offset by 90°. In one embodiment, the offset may be adjustable, though an offset of 90° may lead to optimum results in the three-dimensional position-determination of the marker object. Thus, using the biplane X-ray device (e.g., the biplane C-arm X-ray device), both X-ray planes (e.g., both acquisition assemblies consisting of an X-ray detector and an X-ray source) acquire projection images simultaneously from one angular sub-range each. This provides that the two acquisition assemblies each simultaneously perform a rotational movement over part of the total angular range needed for the reconstruction. The three-dimensional image dataset may then be reconstructed based on the projection images from both acquisition assemblies (e.g., from both X-ray planes).

The marker object may be a high-contrast object that stands out clearly in the image data of the two-dimensional projection images. During acquisition of the projection images, the marker object is located in the region under examination to be acquired. The marker object, as a high-contrast object of image processing, may be localized in the two-dimensional projection images in the most straightforward manner possible. Image processing techniques generally known in the prior art (e.g., segmentation techniques) may be used to localize the marker object. The techniques may localize these marker objects easily in a fully automated manner, especially in the case of high-contrast objects.

Based on the simultaneous acquisition of projection images using different acquisition geometries, there is information available about the marker object from different directions, defined by the projection angles. In other words, the $n^{th}$ projection images $P_A(t_n)$, $P_B(t_n)$ from the acquisition assemblies A and B are acquired simultaneously or extremely quickly in succession at time instant $t_n$. Since the marker object, which is visible both in $P_A(t_n)$ and in $P_B(t_n)$, has been localized by a suitable image processing technique (e.g., image recognition), the three-dimensional position of the marker object at time instant $(t_n)$ may be calculated, likewise automatically, by the relevant geometrical relationships (e.g., epipolar geometry). This therefore exploits the fact that, at least for a specific identifiable point, the information from two (e.g., mutually orthogonal) directions is sufficient to ascertain the three-dimensional position (e.g., effectively to triangulate this position).

Thus, three-dimensional position information about the marker object is then available over all time instants $(t_n)$. The three-dimensional position information describes a motion profile and, if applicable in post-processed form, hence constitutes motion information from which the necessary corrections (e.g., in the individual projection images) may be derived.

The most varied forms of movements may be picked up accurately in this way and described extremely accurately in three dimensions by the motion information. In other words, the present embodiments are not confined to periodic movements of a patient (e.g., respiratory movement), but essentially cover every movement relating to the marker object that takes place in the region under examination. The three-dimensional position information forming the basis of this motion information may be ascertained with great accuracy because simultaneous information from different projection angles is available and is advantageously combined. It is thereby possible to perform high-quality compensation of motion effects on the three-dimensional image dataset ultimately by applying the motion correction such that all the projection images, or at least all the image data of the three-dimensional image dataset, relate to the same motion state in the region under examination. Better three-dimensional image datasets are obtained for acquisitions of moving organs without the need for breath control or other measures.

For biplane X-ray devices (e.g., biplane X-ray devices having two C-arms), the acquisition assemblies are registered with each other since the X-ray device has a common coordinate system, and this registration is needed anyway for many uses, even uses that are different in nature. In addition, the angular positions and suchlike for the C-arms or the acquisition assemblies are generally known in a control device of the X-ray device. Hence, all the information is available for interrelating image information from simultaneously acquired projection images and thus extracting the three-dimensional position information from the two-dimensional location information.

The motion correction may be applied to the individual projection images before reconstructing the three-dimensional image dataset, where, as already described, a specific motion state in the region under examination may be selected. With respect to this, the motion information describes the respective differences, which may be used to correct individual projection images at specific acquisition time instants. Possible ways of performing the motion correction are already generally known in the prior art and therefore do not need to be discussed further here. In addition, motion-correction approaches that address the reconstruction of the three-dimensional image dataset have already been disclosed and may also be applied in the context of the present embodiments.

An anatomical marker object and/or a reference marker additionally provided in or on the patient (e.g., a reference marker of a medical instrument inserted into the patient) may be used as the at least one marker object. Examples of high-contrast objects that may be used as marker objects are, for example, reference markers on a catheter that are radiographically visible, markers on a guide wire that are radiographically visible, endoscope heads, implantable metal objects, accumulations of contrast agent in the body, easily identifiable bone structures, and the like.

In a development, for one or more marker objects of the at least one marker object, at least one orientation of the marker object is determined as part of the position information based on a shape and is included in the motion profile. Additionally or alternatively, given a plurality of marker objects, their relative position information of the plurality of marker objects is used to derive orientation information on at least a portion of the region under examination. In both cases, this hence allows rotations to be taken into account as well as motions in the motion correction. Thus, specifically, a rotational movement may also be modeled in the motion information if the two-dimensional projection images of the marker object may also provide information about the spatial orientation thereof at the respective acquisition time instants. In this regard, shapes for reference markers have already been provided that are intended to allow the orientation to be determined in this way, possibly even just from a single projection image. It is then even possible to compare specific orientations from the pair of projection images with each other. Orientation information is thereby available as part of the position information, with the result that the motion profile describes not just a change in position but also a change in orientation over the acquisition period of the projection images. In other words, the individual pieces of position information may then be ascertained as information describing the pose of the marker object. To a certain extent, rotational movements of portions of the region under examination with respect to one another may also be ascertained if a plurality of marker objects are considered, since in the case of marker objects that do not have a fixed relative position, changes in position that infer a compressive and/or even rotational component of the movements may occur and may be described accordingly.

With regard to determining orientation information for individual marker objects, artificial reference markers (e.g., markers that do not correspond to anatomical structures) may be motion-coupled during the acquisition time to the anatomy of the region under examination, and may not exhibit any intrinsic movements made independently of the anatomy. Thus, for example, the feeding-in of a catheter having reference markers may be suspended briefly, as should similar actions, during the acquisition of the projection images.

The motion profile may be smoothed before performing the motion correction. It is hence possible, for example, to reduce measurement errors or the like, or the impact thereof. Alternatively or additionally, selective outrider detection may be performed, and these outriders may be excluded from consideration. If location information and/or position information is detected to be an outrider and removed, substitute position information may be ascertained for this acquisition time instant (e.g., by interpolation of the motion profile). In one embodiment, the motion profile may be ascertained entirety by interpolation as part of the motion information for the full acquisition period.

In a simple embodiment, in the motion correction, the motion of the marker object is assumed to be the motion of the region under examination. The embodiment is expedient, for example, when the region under examination is a region under examination that moves overall in a substantially uniform manner. If a plurality of marker objects are considered, and if the movement thereof is meant to be interpreted as the movement of the region under examination, statistical processing of the motion profiles of the different marker objects may also be performed (e.g., by averaging). The assumption that the region under examination, or at least the essential anatomical structures in the region under examination, move uniformly with the marker objects may be made, for example, for examinations in the region of bones, but a similar approximation may also be admissible for examinations in the abdomen, where, for example, the respiratory movement has a relatively uniform effect.

In the context of the present embodiments, however, the motion information may also be used to adapt a motion model of the region under examination, where the local individual motion corrections to be performed may be ascertained from the motion model. For example, a biomechanical model may be used as the motion model. The embodiment is suitable particularly when a plurality of marker objects and corresponding motion profiles are detected. The motion information may then be used to drive a motion model (e.g., a biomechanical model) in order to be able to ascertain the motion field of anatomical structures of interest and/or of the region under examination in general. In particular, using a motion model also allows the interpolation of motions of points in the region under examination that are remote from the marker object(s). Using the motion model is expedient, for example, when body regions/regions under examination are being considered that move in a particularly non-uniform manner.

The present embodiments may be used if the projection images are acquired for the purpose of monitoring and/or preparing and/or post-processing a minimally invasive intervention on the patient. In this context, particular advantages have been demonstrated when performing an endoscopic retrograde cholangio-pancreatography (ERCP). High-quality three-dimensional image data is extremely useful especially in minimally invasive interventions, in which, for example, observing progress of a treatment and/or correct positioning of implants and/or of other medical instruments is also involved.

The present embodiments relate not only to the method but also to a biplane X-ray device including two acquisition assemblies (e.g., each arranged on a C-arm, and each including an X-ray source and an X-ray detector) and to a control device configured to implement the method according to one or more of the present embodiments. The control device includes, for example, at least one processor and at least one storage device. For example, the control device, in order to perform the method according to one or more of the present embodiments, may include, in addition to a conventional acquisition unit for controlling the acquisition of two-dimensional projection images along predetermined acquisition trajectories covering the angular ranges, a localization unit for localizing the at least one marker object, a determination unit for ascertaining the position information, an ascertainment unit for ascertaining the motion information, and a correction unit for motion correction of the image dataset (e.g., of the individual projection images prior to reconstruction). Further function units may additionally be provided (e.g., relating to different embodiments).

All the embodiments relating to the method apply analogously to the biplane X-ray device. This device may be a biplane X-ray device having two C-arms, with one of the acquisition assemblies being arranged on each of the C-arms.

A computer program according to one or more of the present embodiments may be loaded, for example, directly into a memory of a control device of a biplane X-ray device, and includes program code (e.g. instructions) to perform the acts of a method when the computer program is executed in the control device of the biplane X-ray device. The computer program may be stored on an electronically readable data storage medium (e.g., a non-transitory computer-readable storage medium) according to one or more of the present embodiments. The computer-readable storage medium therefore includes electronically readable control information stored thereon that includes at least one computer program and is configured to perform a method according to one or more of the present embodiments when the data storage medium is used in a control device of a biplane X-ray device. The data storage medium may be, for example, a non-transient data storage medium such as a CD-ROM.

DETAILED DESCRIPTION

Figure 1:
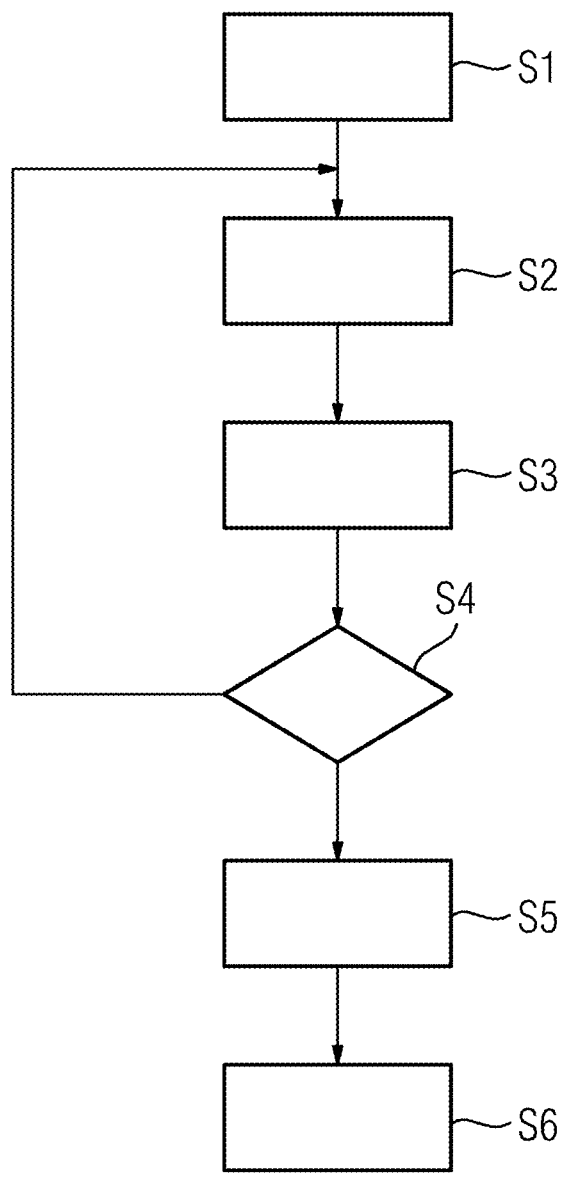
FIG. 1 is a flow diagram of an exemplary embodiment of a method.

FIG. 1 shows a flow diagram of an exemplary embodiment of a method. The intention in the present example is to carry out a minimally invasive intervention (e.g., endoscopic retrograde cholangio-pancreatography) that seeks to reconstruct from two-dimensional projection images from a biplane X-ray device used here, for example, three-dimensional image datasets for a region under examination of a patient. To do this, the projection images are acquired in act S1. For this purpose, in the present exemplary embodiment, the acquisition assemblies of the biplane X-ray device, which each include an X-ray source and an X-ray detector, are coupled to each other at an angle of 90°. Then, by virtue of co-rotation of the C-arms that carry the acquisition assemblies, both acquisition assemblies simultaneously sweep through a particular angular range of projection angles that may be covered by the acquisition assembly concerned. The total angular range obtained by combining the angular ranges is sufficient for reconstructing the three-dimensional image dataset.

Specifically, in act S1, two-dimensional projection images are acquired simultaneously by both acquisition assemblies at each acquisition time instant, hence resulting in pairs of projection images that have been acquired at the same acquisition time instant but in acquisition geometries for which the projection angles are offset by 90°.

Before reconstructing the three-dimensional image dataset from the two-dimensional projection images, however, motion correction may be performed (e.g., directly in the two-dimensional projection images). This is done by using a marker object inside the region under examination of the patient. The marker object is characterized by high contrast with respect to the surrounding anatomical structures, and may itself be an anatomical structure (e.g., a clearly identifiable bone, or else a medical instrument, such as an implant, or a radiopaque reference marker arranged thereon, such as a reference marker on an endo scope being used for endoscopic retrograde cholangio-pancreatography). The endoscope head may also serve as the marker object in this case. Since the marker object for each pair of projection images acquired at one acquisition time instant is imaged from different directions, three-dimensional location information about the marker object may be ascertained for this acquisition time instant by using the epipolar geometry.

Figure 2:
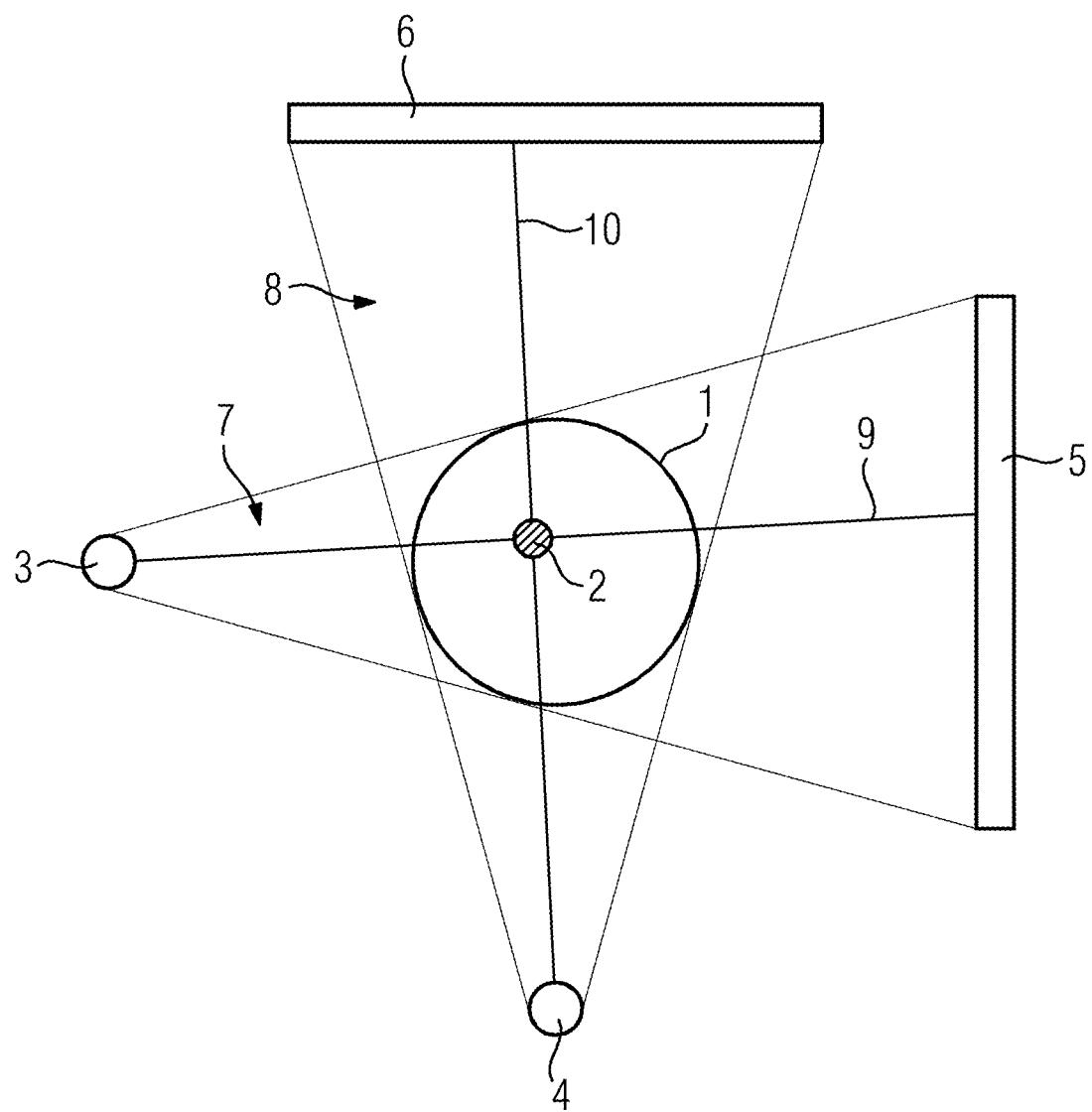
FIG. 2 is a schematic diagram explaining the principle of determining position information.

This is shown schematically in FIG. 2. The figure shows the region under examination 1 of the patient, inside which the marker object 2 is located. In addition, FIG. 2 shows the two acquisition assemblies including respective X-ray sources 3, 4 and respective X-ray detectors 5, 6. The respective radiation fields 7, 8 are also shown. The marker object 2 is imaged at specific positions in the respective projection images of the X-ray detectors 5, 6, as shown by the projection lines 9 and 10 (e.g., corresponding to ray paths).

If these two-dimensional positions in the respective projection images of a pair at an acquisition time instant are known, then corresponding three-dimensional position information may be determined from the acquisition geometries, which are also known to the control device of the X-ray device.

This takes place in acts S2 and S3 in the flow diagram shown in FIG. 1. In act S2, image processing techniques are used (e.g., segmentation techniques) in order to localize in the projection images of a pair, the marker object 2 constituting a high-contrast object, and hence obtain two-dimensional location information about the marker object 2 for both projection images. Optionally, for example, if the shape of the marker object 2 permits this, orientations of the marker object 2 may also be derived for this acquisition time instant from the two-dimensional location information for both projection images jointly, although possibly also from the localization data for each individual projection image.

In an act S3, the three-dimensional position information for the marker object 2 is ascertained by epipolar geometry, as explained, essentially in simple terms by backprojection along the rays 9, 10 and locating the point of intersection. If an orientation has also been ascertained, this may likewise be ascertained as part of the three-dimensional position information for the acquisition time instant, with the result that the three-dimensional position information describes a full pose of the marker object 2.

Acts S2 and S3 may also be performed for a plurality of marker objects 2 if this is required and there are a sufficient number of such automatically detectable marker objects 2 available. Using epipolar geometry or other methods from the prior art, it is possible in this case, should the projections of the plurality of marker objects 2 be indistinguishable in the individual projection images, to assign the associated correspondences.

An act S4 checks whether three-dimensional position information is to be determined for additional acquisition time instants (e.g., for additional pairs of simultaneously acquired projection images). If this is the case, acts S2, S3 are repeated for the next pair of projection images. If, however, all the acquisition time instants have been processed, the method continues to act S5.

In this act, the three-dimensional position information for different acquisition time instants is now used as the basis for ascertaining motion information describing a motion profile of the marker object 2 over the acquisition period (e.g., over the time period in which the acquisition time instants lie). It is intended in this case to smooth the motion profile obtained from the individual acquisition time instants and/or to detect outriders and remove the relevant outriders.

If it is now assumed that the region under examination moves uniformly, the motion (e.g., smoothed and cleaned of erroneous measurements) of the marker object 2 may be assumed to be the motion of the entire region under examination 1. If then a plurality of marker objects 2 are considered, the motion profiles of the marker objects may be combined statistically into an average motion profile as the motion information.

For regions under examination 1 in which sub-regions may move with respect to one another, a motion model (e.g., a biomechanical model) may be parameterized as the motion information. In this case, a plurality of marker objects 2 may then be considered. The motion model then returns a motion state for each point inside the region under examination 1 and for each acquisition time instant.

In act S6, the motion information may then be used to perform the motion correction (e.g., for each acquisition time instant) on the associated two-dimensional projection images. For example, this involves specifying a reference motion state, and the motion information defines the differences from this reference state for each acquisition time instant so that the image data for the projection images may be corrected accordingly. If orientations have been determined as well, these may likewise constitute part of the motion information and be taken into account accordingly.

Once the correction of the projection images in act S6 has been completed, a three-dimensional (3D) image dataset for the region under examination 1 may be reconstructed. The 3D image dataset is of particularly high quality as a result of the prevention, or at least reduction, of motion artifacts.

Figure 3:
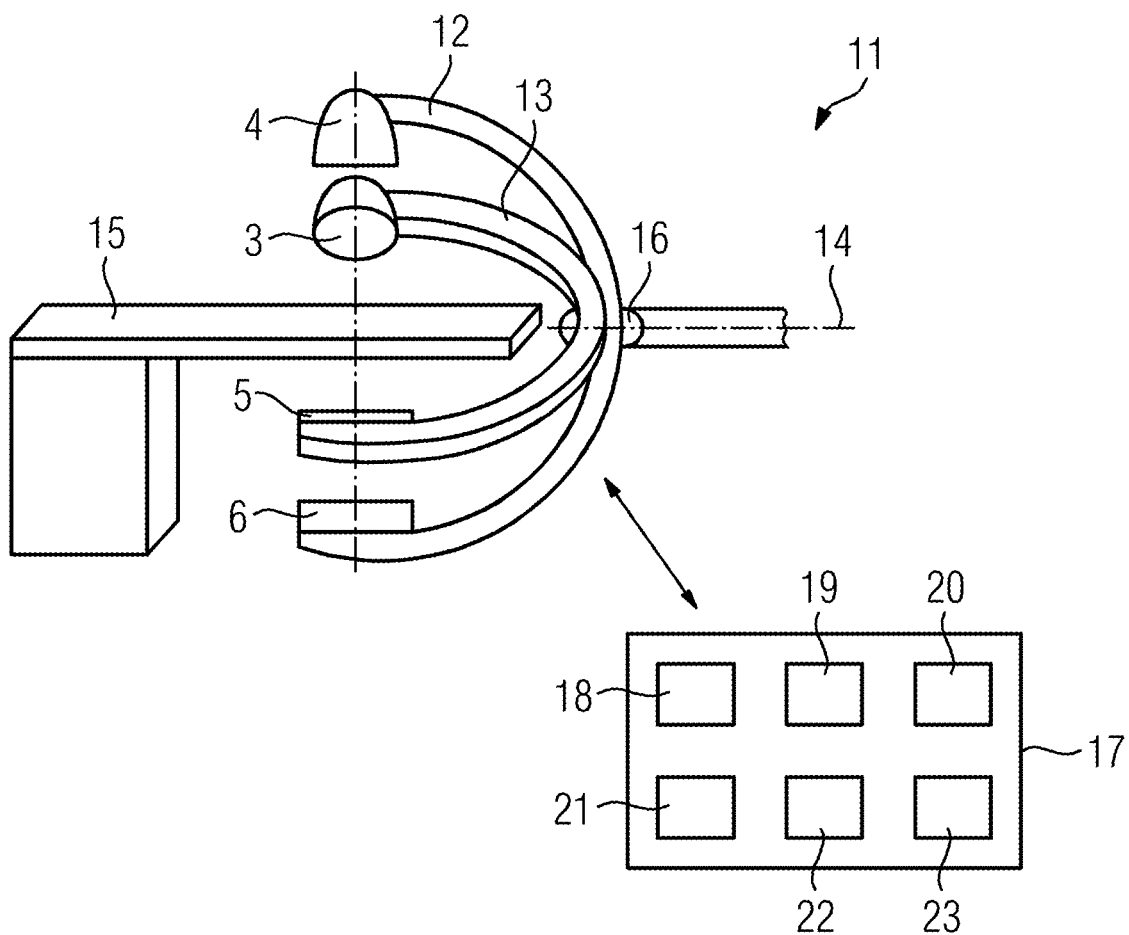
FIG. 3 shows a biplane X-ray device according to an embodiment.

FIG. 3 shows a schematic diagram of one embodiment of a biplane X-ray device 11. As shown, this biplane X-ray device 11 includes two C-arms 12, 13 for associated acquisition assemblies including X-ray sources 3, 4 and X-ray detectors 5, 6. The C-arms 12, 13 may pivot about an axis of rotation 14 jointly or in a coupled manner about a patient table 15, for which purpose a suitable actuating system 16 is provided.

The operation of the biplane X-ray device 11 is controlled by a control device 17 (e.g., a controller) that is configured to implement the method according to one or more of the present embodiments. For this purpose, the control device 17 also includes, in addition to an acquisition unit 18, for example, a localization unit 19 for implementing act S2, a determination unit 20 for implementing act S3, an ascertainment unit 21 for implementing act S5, and a correction unit 22 for implementing act S6. A reconstruction unit 23 for reconstructing the three-dimensional image dataset from the suitably corrected projection images is also provided.

Although the invention has been illustrated and described in detail using the exemplary embodiments, the invention is not limited by the disclosed examples, and a person skilled in the art may derive other variations therefrom without departing from the scope of protection of the invention.

The elements and features recited in the appended claims may be combined in different ways to produce new claims that likewise fall within the scope of the present invention. Thus, whereas the dependent claims appended below depend from only a single independent or dependent claim, it is to be understood that these dependent claims may, alternatively, be made to depend in the alternative from any preceding or following claim, whether independent or dependent. Such new combinations are to be understood as forming a part of the present specification.

While the present invention has been described above by reference to various embodiments, it should be understood that many changes and modifications can be made to the described embodiments. It is therefore intended that the foregoing description be regarded as illustrative rather than limiting, and that it be understood that all equivalents and/or combinations of embodiments are intended to be included in this description.

The invention claimed is:

1. A method for motion correction of a three-dimensional (3D) image dataset reconstructed from a plurality of two-dimensional (2D) projection images acquired by a biplane X-ray device, the motion correction relating to a movement in a region under examination of a patient that is covered by the 3D image dataset, the method comprising:
    using the biplane X-ray device having two acquisition assemblies that measure at an angular offset;
    acquiring the plurality of 2D projection images, the acquiring of the plurality of 2D projection images comprising covering, with each of the two acquisition assemblies, an angular range of projection angles and acquiring pairs of projection images of the region under examination at least substantially simultaneously at each acquisition time instant;
    automatically localizing, for each of the pairs of projection images, at least one marker object lying in the region under examination and imaged in the plurality of projection images, such that 2D location information is determined;
    determining 3D position information about the at least one marker object using acquisition geometries of the respective pair of projection images, the acquisition geometries being defined by the projection angles;
    determining, for one or more marker objects of the at least one marker object, at least one orientation of the one or more marker objects as part of the 3D position information based on a shape, the at least one orientation of the one or more marker objects being included in the motion profile, when the at least one marker object includes a plurality of marker objects, deriving orientation information on at least a portion of the region under examination as part of the 3D position information using relative position information for the plurality of marker objects, or a combination thereof;
    ascertaining motion information describing a motion profile of the at least one marker object over an acquisition period from the determined 3D position information at different acquisition time instants; and
    using the ascertained motion information for motion correction of the 3D image dataset.

2. The method of claim 1, wherein an anatomical marker object, a reference marker, or the anatomical marker object and the reference marker additionally provided in or on the patient is used as the at least one marker object.

3. The method of claim 2, wherein a reference marker of a medical instrument inserted into the patient is used as the at least one marker object.

4. The method of claim 1, further comprising smoothing the motion profile before performing the motion correction.

5. The method of claim 1, further comprising:
    adapting a motion model of the region under examination using the motion information; and
    ascertaining local individual motion corrections to be performed from the motion model.

6. The method of claim 5, wherein a biomechanical model is used as the motion model.

7. The method of claim 1, wherein the plurality of 2D projection images are acquired for the purpose of monitoring, preparing, post-processing, or any combination of monitoring, preparing, and post-processing a minimally invasive intervention on the patient.

8. The method of claim 7, wherein the minimally invasive intervention on the patient is an endoscopic retrograde cholangio-pancreatography.

9. A biplane X-ray device comprising:
two acquisition assemblies; and
a controller configured for motion correction of a three-dimensional (3D) image dataset reconstructed from a plurality of two-dimensional (2D) projection images acquired by the biplane X-ray device, the motion correction relating to a movement in a region under examination of a patient that is covered by the 3D image dataset, the motion correction comprising:
measurement, by the two acquisition assemblies, at an angular offset;
acquisition of the plurality of 2D projection images, the acquisition of the plurality of 2D projection images comprising coverage, with each of the two acquisition assemblies, of an angular range of projection angles and acquisition of pairs of projection images of the region under examination at least substantially simultaneously at each acquisition time instant;
automatic localization, for each of the pairs of projection images, of at least one marker object lying in the region under examination and imaged in the plurality of projection images, such that 2D location information is determined;
determination of 3D position information about the at least one marker object using acquisition geometries of the respective pair of projection images, the acquisition geometries being defined by the projection angles;
determination, for one or more marker objects of the at least one marker object, at least one orientation of the one or more marker objects as part of the 3D position information based on a shape, the at least one orientation of the one or more marker objects being included in the motion profile, when the at least one marker object includes a plurality of marker objects, derivation of orientation information on at least a portion of the region under examination as part of the 3D position information using relative position information for the plurality of marker objects, or a combination thereof;
ascertainment of motion information describing a motion profile of the at least one marker object over an acquisition period from the determined 3D position information at different acquisition time instants; and
use of the ascertained motion information for motion correction of the 3D image dataset.

10. The biplane X-ray device of claim 9, wherein the two acquisition assemblies are each arranged on a C-arm.

11. A non-transitory computer-readable storage medium that stores instructions executable by one or more processors to motion correct a three-dimensional (3D) image dataset reconstructed from a plurality of two-dimensional (2D) projection images acquired by a biplane X-ray device, the motion correction relating to a movement in a region under examination of a patient that is covered by the 3D image dataset, the instructions comprising:

using the biplane X-ray device having two acquisition assemblies that measure at an angular offset;
acquiring the plurality of 2D projection images, the acquiring of the plurality of 2D projection images comprising covering, with each of the two acquisition assemblies, an angular range of projection angles and acquiring pairs of projection images of the region under examination at least substantially simultaneously at each acquisition time instant;
automatically localizing, for each of the pairs of projection images, at least one marker object lying in the region under examination and imaged in the plurality of projection images, such that 2D location information is determined;
determining 3D position information about the at least one marker object using acquisition geometries of the respective pair of projection images, the acquisition geometries being defined by the projection angles;
determining, for one or more marker objects of the at least one marker object, at least one orientation of the one or more marker objects as part of the 3D position information based on a shape, the at least one orientation of the one or more marker objects being included in the motion profile, when the at least one marker object includes a plurality of marker objects, deriving orientation information on at least a portion of the region under examination as part of the 3D position information using relative position information for the plurality of marker objects, or a combination thereof;
ascertaining motion information describing a motion profile of the at least one marker object over an acquisition period from the determined 3D position information at different acquisition time instants; and
using the ascertained motion information for motion correction of the 3D image dataset.

12. The non-transitory computer-readable storage medium of claim 11, wherein an anatomical marker object, a reference marker, or the anatomical marker object and the reference marker additionally provided in or on the patient is used as the at least one marker object.

13. The non-transitory computer-readable storage medium of claim 12, wherein a reference marker of a medical instrument inserted into the patient is used as the at least one marker object.

14. The non-transitory computer-readable storage medium of claim 11, wherein the instructions further comprise smoothing the motion profile before performing the motion correction.

15. The non-transitory computer-readable storage medium of claim 11, wherein the instructions further comprise:
adapting a motion model of the region under examination using the motion information; and
ascertaining local individual motion corrections to be performed from the motion model.

16. The non-transitory computer-readable storage medium of claim 15, wherein a biomechanical model is used as the motion model.

* * * * *